(12) United States Patent
Curiel et al.

(10) Patent No.: US 6,683,170 B2
(45) Date of Patent: Jan. 27, 2004

(54) LIGANDS ADDED TO ADENOVIRUS FIBER

(75) Inventors: David T. Curiel, Birmingham, AL (US); Jeffrey A. Engler, Birmingham, AL (US)

(73) Assignee: UAB Research Foundation, Birmingham, AL (US)

(*) Notice: Subject to any disclaimer, the term of this patent is extended or adjusted under 35 U.S.C. 154(b) by 36 days.

(21) Appl. No.: 09/904,599

(22) Filed: Jul. 13, 2001

(65) Prior Publication Data

US 2002/0076419 A1 Jun. 20, 2002

Related U.S. Application Data

(62) Division of application No. 08/218,369, filed on Mar. 28, 1994, now Pat. No. 6,312,699.

(51) Int. Cl.[7] ............................................... C07H 21/04
(52) U.S. Cl. ................. 536/24.2; 435/69.1; 435/320.1; 435/235.1; 435/325; 435/440; 536/23.1; 536/23.72; 536/24.2
(58) Field of Search ...................... 536/23.1; 435/320.1, 435/235.1, 325, 440

(56) References Cited

PUBLICATIONS

Hong et al. Virology, 1991, vol. 186, pp. 758–767.*

* cited by examiner

*Primary Examiner*—David Guzo
*Assistant Examiner*—M Marvich
(74) *Attorney, Agent, or Firm*—Benjamin Aaron Adler

(57) ABSTRACT

The fiber protein of adenovirus has been genetically altered via attachment at the carboxyl end of a peptide linker, preferably up to 26 amino acids in length which forms a random coil, which can be used to attach a non-adenovirus ligand altering the binding specificity of the fiber protein. Examples of ligands include peptides which are selectively bound by a targeted cell so that the modified fiber protein is internalized by receptor-mediated endocytosis, and peptides which can act as an universal coupling agent, for example, biotin or strepavidin. The linker is designed to not interfere with normal trimerization of fiber protein, to avoid steric hindrance of binding of the fiber protein to a targeted cell, and to serve as a site to introduce new peptide sequence.

9 Claims, 2 Drawing Sheets

LIGANDS ADDED TO ADENOVIRUS FIBER

This is a divisional application of U.S. Ser. No. 08/218,369 filed on Mar. 28, 1994, now U.S. Pat. No. 6,312,699.

BACKGROUND TO INVENTION

The present invention generally relates to modification of the adenovirus fiber protein and methods for use thereof to modify cellular attachment by the fiber protein.

In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis is reviewed by Brown and Greene, *DNA and Cell Biology* 1991 10:6, 399–409. A number of viruses infect cells via a receptor-ligand interaction. Adenovirus is an example of a virus that utilizes receptor-mediated endocytosis to internalize infectious virus.

Gene therapy requires transfer of recombinant nucleic acid constructs into cells. Although a number of different methods for gene transfer have been proposed, one of the most promising remains by utilizing recombinant viruses. The development of recombinant adenoviruses for this purpose has had a number of applications, based upon the unique advantages of this system.

One advantage is that recombinant adenoviruses have been isolated and characterized that contain genomic deletions that render the virus replication incompetent except within cell lines that trans-complement the deleted functions. The cell lines that contain the viral genes required for production of infective viral particles are called packaging cell lines. The construction of the replication-defective adenoviruses is described by Berkner et al., 1987 *J. Virology* 61:1213–1220 (1987); Massie et al., 1986 *Mol. Cell. Biol.* 6:2872–2883 (1986); Haj-Ahmad et al., 1986 *J. Virology* 57:267–274 (1986); Davidson et al., 1987 *J. Virology* 61:1226–1239 (1987); Zhang "Generation and identification of recombinant adenovirus by liposome-mediated transfection and PCR analysis" *BioTechniques* 1993 15:868–872. The benefit of the use of these viruses as vectors is that they are limited in the extent to which they can spread to other cell types, since they can replicate within an initial infected cell, but are unable to form new infectious viral particles.

The ability of the virus to achieve high levels of expression of therapeutic gene products, and the capacity of the virus to infect non-dividing, terminally differentiated cells, has been exploited for gene therapy applications requiring direct, in vivo gene delivery. Recombinant adenoviruses have been shown to achieve high efficiency gene transfer after direct, in vivo delivery to airway epithelium, hepatocytes, vascular endothelium, CNS parenchyma and a number of other tissue sites, as reported by Morsy, 1993 *J. Clin. Invest.* 92:1580–1586; Kirshenbaum, 1993 *J. Clin. Invest.* 92:381–387; Roessler, 1993 *J. Clin. Invest.* 92:1085–1092; Moullier, 1993 *Nature Genetics* 4:154–159; La Salle, 1993 *Science* 259:988–990; Gomez-Foix, 1992 *J. Biol. Chem.* 267:25129–25134; Rich, 1993 *Human Gene Therapy* 4:461–476; Zabner, 1994 *Nature Genetics* 6:75–83; Guzman, 1993 *Circulation Research* 73:1201–1207; Bout, 1994 *Human Gene Therapy* 5:3–10; Zabner, 1993 *Cell* 75:207–216; Caillaud, 1993 *Eur. J. Neuroscience* 5:1287–1291; and Ragot, 1993 *J. Gen. Virology* 74:501–507.

Whereas the broad tropism of the adenovirus has allowed transduction of a variety of tissue types for certain gene therapy applications, this broad host range may also create additional problems. It is generally recognized that in the context of direct in vivo gene delivery, the ability to target heterologous genes to specific cellular targets would be highly advantageous, as reviewed by Anderson, 1992 *Science* 256:808–813; McCabe, 1993 *Biochemical Medicine and Metabolic Biology* 50:241–253. The promiscuous tropism of the adenovirus could potentially undermine those strategies where cell-specific delivery is essential. In this regard, it has been shown that systematically administered adenovirus transduces multiple tissue types (Stratford-Perricaudet, 1992 *J. Clin. Invest.* 90:626–630). This non-specific delivery could be potentially deleterious, since ectopic expression of transferred, heterologous genes could occur in inappropriate cellular targets as a result. Furthermore, the ubiquitous binding of the virus may require systemic administration of prohibitive doses of virus in order to adequate transduce a specific target site in vivo.

In addition to the binding of a broad virus tropism in vivo, the lack of adenovirus binding to a given target cell may obviate the utility of this vector for some gene therapy applications. For example, for mature differentiated muscle cells, the lack of a receptor for adenovirus prevents use of adenoviral gene transfer strategies for targeting this tissue type, as reviewed by Ragot, 1993; and Karpati, 1993 *Muscle and Nerve* 16:1141–1153). Thus, it would be useful in certain instances to broaden the tropism of recombinant adenovirus to allow gene delivery to selected cell subsets not presently transducible with this vector system.

Recombinant adenoviruses achieve gene transduction by binding to specific cell surface receptors, after which the virus is internalized by receptor-mediated endocytosis, in the same manner as wild type or replication-defective adenovirus, as reported by Chardonnet and Dales, 1970 *Virology* 40:462–477; Brown and Burlingham, 1973 *J. Virology* 12:386–396; Svensson and Persson, 1985 *J. Virology* 55:442–449; Seth, et al., 1984 *J. Virol.* 51:650–655; Seth, et al., *Mol. Cell. Biol.* 1984 4:1528–1533; Varga et al., 1991 *J. Virology* 65:6061–6070 (1991); Wickham et al., 1993 *Cell* 73:309–319). The adenovirus binds to the receptor via the knob portion of the fiber protein that projects outward from the viral coat. The fiber protein is actually a homotrimeric protein encoded by the fiber gene within the adenoviral genome. Adenovirus capsid proteins, which include the hexon, penton base, and fiber proteins, are synthesized late in infection in the cytoplasm and transported to the nucleus for assembly into virus particles.

Fiber plays a crucial role in adenovirus infection by attaching the virus to a specific receptor on the cell surface. The fiber consists of three domains: an N-terminal tail that interacts with penton base, a shaft composed of 22 repeats of a 15 amino acid segment that forms β-sheet and β-bends, and a knob at the C-terminus that contains the type-specific antigen and is responsible for binding to the cell surface receptor. The fiber protein is also responsible for transport of viral nucleic acids into the nucleus. The gene encoding the fiber protein from adenovirus serotype 2 has been expressed in human cells and shown by using a recombinant vaccinia virus vector to be correctly assembled into trimers, glycosylated and transported to the nucleus, as reported by Hong and Engler, 1991 *Virology* 185, 758–767.

Alteration of gene delivery mediated by recombinant adenovirus to specific cell types would have great utility for a variety of gene therapy applications.

It is therefore an object of the present invention to provide a method and means by which adenovirus can be targeted to infect specific cell types.

It is a further object of the present invention to provide a method and means by which adenovirus proteins can be used to target nucleic acid or protein delivery to a specific cell or the nucleus of a specific cell.

SUMMARY OF THE INVENTION

The fiber protein of adenovirus has been genetically altered via attachment at the carboxyl end of a peptide linker, preferably up to 26 amino acids in length which forms a random coil, which can be used to attach a non-adenovirus ligand altering the binding specificity of the fiber protein. Examples of ligands include peptides which are selectively bound by a targeted cell so that the modified fiber protein is internalized by receptor-mediated endocytosis, and peptides which can act as an universal coupling agent, for example, biotin or strepavidin. The linker is designed to not interfere with normal trimerization of fiber protein, to avoid steric hindrance of binding of the fiber protein to a targeted cell, and to serve as a site to introduce new peptide sequence. The modified fiber protein is prepared by genetic engineering of the nucleotide sequence encoding the fiber protein, through the addition of new sequence at the carboxyl tail-encoding region which encodes the linker and the ligand. The N-terminus of the fiber protein is not altered in the preferred embodiment, although in some embodiments it may be desirable to inhibit uptake by the nucleus of the fiber protein, by deletion of nuclear targeting signals.

The modified fiber protein can be utilized as part of a recombinant adenovirus for use in gene therapy.

DETAILED DESCRIPTION OF THE INVENTION

Figure 1:
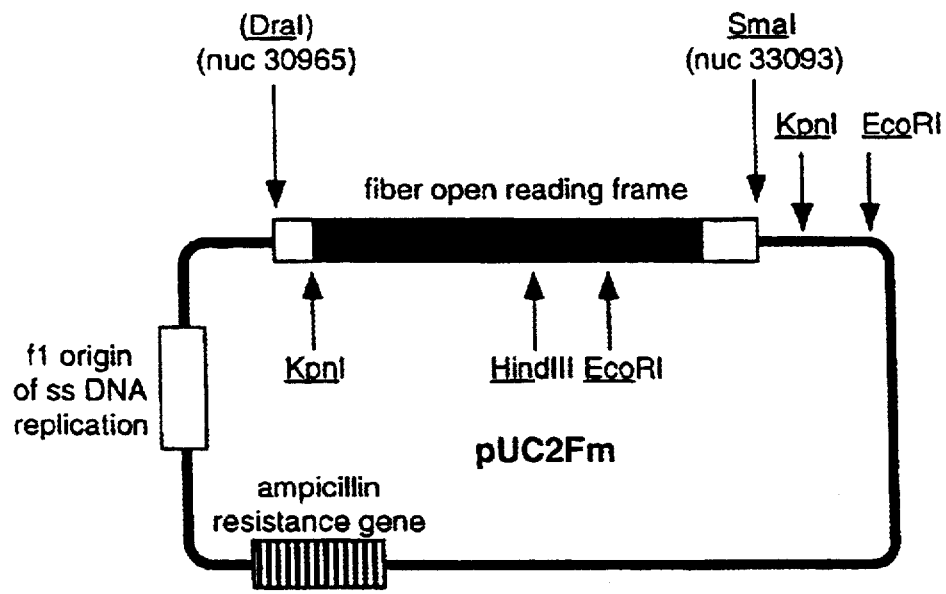
FIG. 1 is schematic of a plasmid pUC2Fm for mutagenesis of the adenovirus 2 fiber gene. Restriction endonuclease cleavage sites are shown with their standard abbreviations. The fragment from Ad2 virus DNA that encodes the fiber gene, nucleotides 30965 to 33093, was inserted by blunt end ligation into the SmaI cleavage site of pUC119 DNA, resulting in the loss of the DraI cleavage site.
Figure 2:
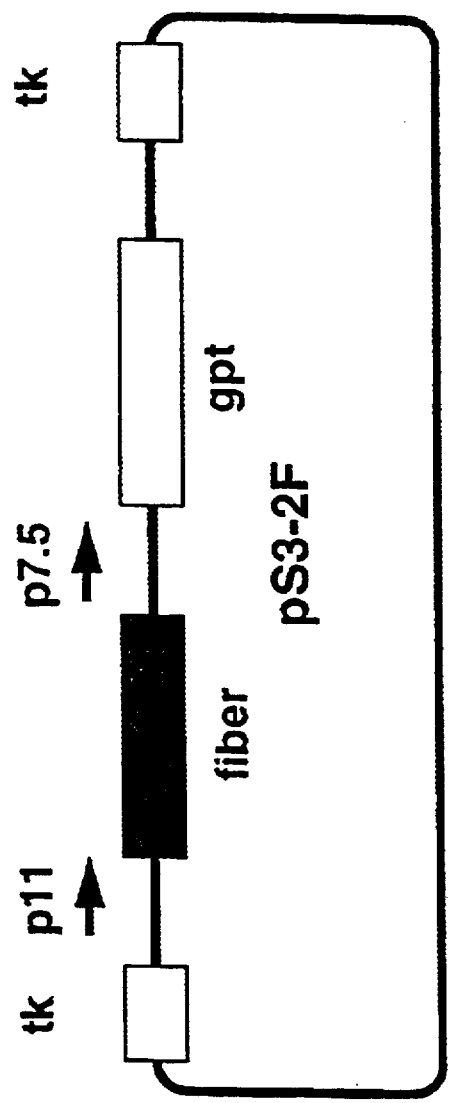
FIG. 2 is a schematic of the plasmid pS32F, described by Falkner and Moss (1988), for expression of fiber mutants in vaccinia virus. The fiber gene or mutants of the fiber gene were cloned into the HpaI cleavage site of the plasmid. Boxes marked "tk" are DNA segments from the vaccinia virus thymidine kinase gene, allowing recombination of the plasmid into the thymidine kinase gene of vaccinia virus.

Alteration of the normal binding of the adenovirus fiber protein is one strategy for modifying the normal tropism of recombinant adenoviruses. The most versatile and cost-effective strategy for modifying the normal adenoviral binding is to genetically modify the knob portion of the fiber protein. Since the fiber protein is a complex glycoprotein requiring assembly into trimers, inappropriate genetic modification of the protein would be expected to interfere with the protein structure-function required for the mature, trimeric, fiber protein. The genetic modulation of the fiber protein are greatly facilitated by the availability of methods for producing glycosylated protein and assessing trimerization. In addition, the development of an easily modified portion of the gene encoding the knob portion of the protein, analogous to a cloning site in a plasmid vector, greatly facilitates future modifications of the knob protein.

The genetic modification of adenovirus binding is a complex process requiring the successful completion of several steps.

The first step was the development of a means to produce normally glycosylated fiber protein separate from the intact adenovirus in amounts sufficient for functional analysis. This step is necessary because the individual gene is more amenable to the genetic modifications described herein, and importantly, because changing the native binding of the adenovirus could interfere with routine propagation of the new virus in cell lines dependent on the normal adenovirus receptor binding. A recombinant vaccinia virus vector was successfully utilized to accomplish this first step. It was found that this system not only resulted in the production of isolated fiber protein, but also made protein that was normally glyscosylated.

Having developed methods for producing the isolated, normally glycosylated fiber protein, the next step was the development of methods to assess the ability of the isolated fiber protein to associate into the homotrimer form as found on the intact adenovirus. This was accomplished by the development of monoclonal antibodies specific for the monomeric or trimer forms of the fiber protein. Western blot analysis of the wild type and native proteins with exposure to the appropriate antibodies demonstrated the presence or absence of trimerization in the modified fiber proteins. This could also be accomplished using SDS polyacrylamide gel electrophoresis (PAGE) based on the molecular weight differences between the fiber protein monomer and trimer.

The third step was the production of a specific linker that would accomplish three goals:
 (a) serving as a site for the introduction of multiple peptide coding sequences;
 (b) presenting the new peptide coding sequences so as to avoid steric hindrance from the structural fiber protein at the knob portion of the fiber protein; and
 (c) not interfering with the normal trimerization of the protein.

As described in detail below, these goals were accomplished by designing a nucleotide sequence coding for a random coil peptide that would permit any ligand to extend beyond the end of the fiber trimer complex. This nucleotide sequence also contains a unique restriction endonuclease site for subsequent introduction of additional peptide sequences designed for the modulation of binding either directly, or by serving as attachment sites for larger proteins that could not be directly integrated into the fiber protein without disturbing the trimerization. Finally, the knowledge of the sites of the fiber protein that could be modified to achieve the desired effect was used to select the site of linker insertion at the carboxy-terminus of the protein.

The fourth step is the insertion of peptide coding sequences within the linker peptide at the carboxyl terminus of the fiber protein. The initial sequences chosen include peptides that serve as universal attachment sites for larger proteins, such as the widely available biotin or avidin-conjugated proteins, and peptides that are internalized by receptor-mediated endocytosis upon binding at the cell surface such as angiotensin II and bombesin. Both classes of peptides can be used to redirect the adenovirus to specific, nonadenoviral receptors, after which the virus is internalized by receptor-mediated endocytosis.

The last step is to reintroduce the modified fiber protein into a recombinant adenoviral genome and produce the modified adenovirus for testing of receptor binding characteristics. Standard techniques are used to reintroduce the modified fiber gene(s) and produce new recombinant virus. The receptor binding of the modified fiber protein is tested with cell lines with known adenoviral receptor-binding characteristics.

The following detailed description and examples demonstrate how these steps have been performed and the resulting modified adenovirus fiber protein and adenovirus containing the modified fiber protein produced. As noted, a number of variations within each step that would yield other modified fiber proteins may be made using the described techniques and materials.

Means to Produce Normally Glycosylated Fiber Protein Separate from the Intact Adenovirus
Expression Systems The recombinant vaccinia virus vector, pTKgpt-3S, described by Falkner, 1988 *J. Virology* 62:1849–1854, can be used to produce the fiber protein in isolation from the remainder of the adenovirus. This vector provides a convenient cloning site for the fiber protein, and includes the *E. coli* gpt gene as a selectable marker for the recombinant vaccinia virus containing the adenoviral fiber gene. Other recombinant vaccinia viral vectors have also been described that could be used; for example, fiber protein has also been expressed in recombinant vaccinia viruses, using the two virus bacteriophage T7 RNA polymerase approach described by Fuerst et al. (1986) *Proc. Nacl. Acad. Sci. USA* 83:8122–8126. Other eukaryotic expression vectors, such as recombinant retroviruses, could also be used to produce normally glycosylated fiber protein in sufficient amounts for functional testing of trimerization.

Selection of Adenovirus Fiber Protein Genes

In the specific examples described here, the human adenovirus type 2 and 5 fiber genes were genetically modified and tested. These were selected because these two adenovirus types are those most commonly in use for gene therapy applications. However, the fiber gene sequences have been described for other human adenoviruses, including type 3, reported by Signas et al., 1986 *Gene* 50:173–184), type 4, reported by Gruber et al., 1993 *Virology* 196:603–611), type 7, reported by Mullis et al., 1988 *Virology* 167:545–553), 11 (Mei and Wadell, 1993 *Virology* 194:453–462), 40 (Kidd et al., 1989 *Virology* 172:134–144; 1993 *Virology* 192:73–84), and 41 (Kidd et al., 1990 *Virology* 179:139–150), the teachings of which are specifically incorporated herein, and the methods described herein could be used for the modification of these other serotype fiber genes as well.

Methods to Assess the Ability of the Isolated Fiber Protein to Associate into the Homotrimer Form
Monoclonal Antibodies The vaccinia-produced fiber protein can be readily tested for trimerization using western blot analysis in conjunction with monoclonal antibodies capable of differentiating between monomeric and trimeric forms of the protein. Two such monoclonal antibodies have been characterized by Hong and Engler, 1991 *Virology* 185:758–767:

1. Antibody 4D2.5 recognizes the amino terminus of both monomeric and trimeric forms of Ad2, Ad5 and Ad7 fiber, both on Western blots and by indirect immunofluorescence.

2. Antibody 2A6.36 recognizes only completely formed Ad2 and Ad5 fiber trimers, by recognizing an epitope between amino acids 17 and 60 of the protein.

Other antibodies can be produced as described by Hong and Engler, using standard techniques.

Using these antibodies, information about the structure of fiber or of fiber mutants can be obtained by both Western blot and by indirect immunofluorescence.

SDS-PAGE

This could also be accomplished using SDS polyacrylamide gel electrophoresis (PAGE) based on the molecular weight differences between the fiber protein monomer and trimer.

As determined using these methods and the antibodies, it is essential that the peptide sequences that are added to the end of the fiber gene open reading frame not disrupt the secondary structure of the fiber protein molecules; i.e., they must still form trimers.

Design and Production of a Specific Peptide Linker
The Linker Peptide

The carboxyl-terminal portion of the fiber protein is modified to include a random coil peptide linker that does not interfere with trimerization. A twelve amino acid peptide sequence: PASASASASPGS (Seq. ID No. 1) could be added to the C-terminus without interrupting formation of the trimer, binding to the cell, and transport into the nucleus. As reported by Hong and Engler (1991), a six amino acid peptide sequence: PKRARP (Seq. ID No. 3) could be added to the C-terminus without interfering with trimerization. However, insertion of a 27 amino acid peptide sequence: RIVNLLHVMFQSVYFSIAENFKSFFIQ (Seq. ID No. 4), which did not form a random coil, at the same location prevented trimerization. Accordingly, the general requirements for the linker are that it must not interfere with trimerization and should form a random coil, and is preferably less than twenty seven amino acids in length.

While any protein sequence that forms a random coil could be used for this strategy, a model sequence: PASASASASPGS (Seq. ID No. 1), was used in the examples described below. Other peptide coding sequences can be selected based on protein structure prediction programs such as PEPPLOT, from the Genetics Computer Group, Madison, Wis. The model sequence was selected using PEPPLOT which predicted that repeating AS motifs will form random coils. The repeating AS motif should also be neither hydrophobic, hydrophilic nor charged, insuring that this protein sequence will provide the maximum flexibility.

Prolines were introduced at each end of the sequence to provide a kink in the protein sequence, so that the random coil domain would be separated both from the fiber sequences and from any subsequently added ligands.

Site for Addition of the Linker

The specific site for addition of the random coil-encoding oligonucleotide was determined based on extensive experimentation. As described in detail in Example 2, the linker is inserted at the carboxyl terminus of the fiber protein.

Insertion of Peptide Coding Sequences within the Linker Peptide
Insertion into Linker Any number of protein ligands can be inserted at the end or within the peptide linker. These are added by inserting a nucleic acid sequence encoding the ligand into an appropriate restriction site in or at the end of the sequence encoding the linker.

Ligands

The linker is coupled to a protein ligand that can be specific to a particular cell type, or serve as a more universal coupler. Examples of specific ligands include any molecule which binds to a specific cell surface receptor, other than the natural receptor for the adenovirus fiber protein, for example, an arginine-glycine-aspartic acid (RGD) peptide, and antibodies and antibody fragments. Examples of universal couplers include biotin and avidin binding proteins that can be used to "couple" other proteins to the fiber protein, which may or may not independently bind to a targeted cell. In a preferred embodiment, the ligand protein sequences serve as an attachment site for avidin or biotin conjugated proteins. Peptide sequences critical for biotin-avidin (streptavidin) binding have been described by Saggio and Laufer, Biochem. J. 1993 293:613–616, Alon 1993 Eur. J. Immunol. 23:893–898, and Hiller, et al., 1991 Biochem. J. 278:573–585. A commercially available nucleic acid encoding a streptavidin binding peptide (Streptag™) is sold by from Biometra, Gottingen, Germany.

These sequences are particularly useful for the convenient attachment of proteins useful for redirecting the adenovirus binding, which could include monoclonal antibodies and specific ligands for cell surface receptors that are too large to conveniently insert via genetic engineering of the fiber protein and linker. It is also possible to attach marker proteins to these sites that are useful for monitoring the distribution and metabolism of adenovirus administered to intact organisms. The binding sites could also be used to isolate the adenovirus or adenovirus components from complex protein mixtures.

Other oligopeptide sequences with peptide binding domains could also be used, such as the Arginine-Glycine-Aspartic Acid (RGD) sequence which binds to vitronectin, described by Cherny, et al., 1993 J. Biol. Chem. 268(13):9725–9729, the RGDS mimicking peptide in strepavidin, arginine-tyrosineaspartic acid-serine (RYDS), described by Alon, et al., 1993, Eur. J. Immunol. 23:893–898, or others determined as described by Kay, et al., 1993 Gene 128:59–65.

Other examples of ligands which can be linked to the fiber protein include those that are internalized upon binding to the cognate receptor by receptor-mediated endocytosis. The rationale is that the virus will be internalized along with the ligand. Examples of peptides that are internalized by receptor-mediated endocytosis after binding a cell surface receptor are the angiotensin II and gastrin-releasing peptides described in the following examples.

However, other ligands that are not internalized by receptor-mediated endocytosis could also be used to target adenoviral-mediated gene transfer to specific cell types. For example, it has been demonstrated that lectins can be used to target adenovirus to cell types with high concentration of the relevant receptors, Batra 1993, even though the lectins are not internalized upon binding to the cell surface.

Expression of the Modified Fiber Protein

After engineering of the fiber protein to produce a modified fiber protein including a linker, or a linker-ligand, the modified fiber protein is screened for trimer formation as described above and for binding to the targeted cell type. Trimer formation can be screened for as described above, using a vaccinia expression system or packaged with recombinant adenovirus. In the preferred embodiment, the modified fiber protein is expressed in mammalian cells. Expression of fiber using recombinant baculovirus in insect cells is not preferred since preliminary data suggested that fiber synthesized in insect cells was underglycosylated. This may also be true of yeast.

Binding of the modified fiber protein can be determined using standard techniques, for example, radiolabelling virus, adding virus to cells, incubating, washing away unbound virus, and measuring radioactivity bound to the cells, or infecting cells with recombinant virus including the modified fiber protein, using a known virus titer, then using a cytopathic assay to screen for lysis (only cells where the virus binds can be infected; infection with adenovirus results in cell death).

Packaging into Recombinant Adenovirus

The modified fiber protein gene is packaged with recombinant adenovirus using standard techniques. In general, adenovirus genes other than the gene for the fiber protein are mixed with the gene encoding the modified fiber protein and cotransduced into cells. There are many methods for transduction of cells with viral material that are known to those skilled in the art, for example, Gene transfer and expression: a laboratory manual Kriegler M. 242 pp. (W. H. Freeman, NY 1991); and Current Protocols in Molecular Biology. 1987–1994, Ausubel F. M., et al., section entitled "Introduction of DNA into Mammalian Cells" pp. 9.0.1–9.17.2 (John Wiley & Sons). In a preferred example of a transduction enhancer, cationic lipids that are commonly modified phospholipids to obtain a positive charge are used for transduction of the first and second. A number of lipid compounds shown to have efficacy for nucleic acid transduction, for example, the cationic lipid N-[1-(2,3-Dioleoyloxy)propyl]N,N,N-trimethyl-ammoniummethylsulfate (DOTAP) can be used. The stock solution commercially obtained from Boehringer Mannheim is diluted three-fold with HEPES buffered saline and mixed with DNA at 50 ng/µl. The typical ratio of lipid to DNA (weight:weight) is 6:1, but other ratios may provide better results as determined by empiric testing. After allowing the DNA and lipid to associate for 10 minutes, the lipid-DNA complexes are administered to the target cells. The precise conditions for the cotransduction can be easily established by those skilled in the art using the teachings provided here.

The packaged recombinant adenoviral genome containing the gene encoding the modified fiber protein are then tested for receptor binding characteristics and usefulness for gene therapy as described above. Although any system, including the vaccinia virus expression system as well as recombinant adenovirus, can be used for screening of the binding characteristics of the modified fiber protein, it is preferred to use recombinant adenovirus for gene therapy.

Addition of Genes for Gene Therapy

"Gene therapy" refers to the treatment of pathologic conditions by the addition of exogenous nucleic acids to appropriate cells within the organism. Nucleic acids must be added to the cell, or transduced, such that they remain functional within the cell. For most gene therapy strategies, the new nucleic acids are designed to function as new genes, i.e., code for new messenger RNA that in turn codes for new protein. As originally conceived, gene therapy was directed towards monogenetic disorders like adenosine deaminase deficiency and cystic fibrosis. It has become abundantly clear that gene therapy might also be helpful in polygenetic somatic disorders like cancer.

Nucleic acids useful for gene therapy include those that code for proteins used to identify cells infected with the recombinant virus, those that encode for proteins that function to kill cells containing the viral genome, or that encode for therapeutic proteins that will serve to treat a pathophysiologic condition within the body.

The sequences that encode for many of these proteins are known and published in the literature. Representative marker genes include those described in detail in the following examples, including an enzyme such as β galactosidase and proteins conferring antibiotic resistance or susceptibility. Other examples include proteins that augment or suppress abnormal proteins, as well as those that are toxic or deleterious to abnormal cells within the body. One example of the latter is the herpes simplex virus thymidine kinase gene. The addition of ganciclovir to cells expressing this gene results in death of the cell. Still others are those which are defective or missing in the patient to be treated, for example, the cystic fibrosis transmembrane regulator gene ("CFTR") can be added to cells containing mutant CFTR with subsequent correction of the ion transport defect caused by the mutant CFTR gene. Examples of other genes currently being investigated for use in gene therapy include adenosine deaminase, insulin, coagulation factors such as factor VIII, and glycogen degrading enzymes.

Although the sequences incorporated into the recombinant virus will typically be nucleic acids encoding proteins, the sequences themselves may also be biologically active. Many examples of such materials are known, for example, antisense and ribozymes. Unless specifically stated otherwise, the genes encode therapeutic molecules including biologically active nucleic acids, nucleic acids encoding biologically active proteins, and nucleic acids encoding proteins responsible for producing the biologically active molecules of interest, whether protein or other type of molecule.

For example, for human gene therapy use, one of the viral nucleic acid constructs could be modified to contain a "suicide gene" so that the virus producing cells could be eliminated as desired. As one specific example, the viral genome could include herpes simplex virus thymidine kinase coding sequences. It is well established that cells expressing the viral thymidine kinase gene product can be eliminated by treatment with the antiviral agent, ganciclovir (Moolten 1986 *Cancer Research* 46:5276). In this manner, the virus producing cells would be eliminated by systemic administration of FDA-approved ganciclovir.

The present invention will be further understood by reference to the following non-limiting examples. The teachings of the references described herein are specifically incorporated by reference, as they relate to the enablement of the claimed subject matter.

EXAMPLE 1

Production of Useful Amounts of Glycosylated Wild Type and Mutant Fiber Proteins a. Preparation of Ad2 and Ad5 Fiber Genes for Cloning and Mutagenesis Adenovirus DNA was purified from adenovirus virions that had been purified by CsCl banding of cell lysates of infected HeLa cells; DNA was released from the purified virions by treating with 0.5% SDS and 1 mg/ml proteinase K for 1 hour at 37° C., followed by phenol extraction. A DraI-SmaI restriction endonuclease cleavage product (containing Ad2 nucleotides 30965 to 33093, available from GenBank, National Library of Medicine, National Institutes of Health, file ADRCG.viral) was purified on an agarose gel, extracted by electrophoresis onto DEAE membrane, and cloned into the vector pUC119 at the SmaI restriction cleavage site in the polylinker. Single-strand DNA containing the fiber gene was made by infecting bacteria containing this plasmid with an M13 helper phage (K07, Stratagene, San Diego, Calif.) and isolating the resulting phage DNA, according to the manufacturer's instructions. Site-directed mutagenesis (Zoller and Smith, 1983) with the oligonucleotide 5' GGCGCGTTTCATGGTACCTGCAACAA 3' (Seq. ID No. 2) was used to create a KpnI restriction endonuclease cleavage site at nucleotide 31024, so that the resulting fragment could be removed by digestion with KpnI (or its isoschizomer Asp718), by cleavage at the newly created KpnI site at the beginning of the fiber gene open reading frame and at a KpnI cleavage site in the polylinker of pUC119 beyone the 5' end of the fiber gene. The correct mutant was verified by DNA sequencing of the plasmid DNA and by the restriction endonuclease cleavage pattern after digestion with KpnI or with Asp718, which released a 2075 base pair fragment that could be identified on an agarose gel.

b. Preparation of Mutated Fiber Genes

One of the advantages of cloning the Ad2 and the Ad5 fiber genes into pUC119 is that site-directed mutagenesis, described by Zoller and Smith, 1983 "Oligonucleotide-directed mutagenesis of DNA fragments cloned into M13 vectors". In *Methods in Enzymology*, R. Wu, L. Grossman and K. Moldave, Eds., vol. 100, pp. 468–500 (Academic Press, New York), can be easily accomplished, using single-stranded DNA prepared as described above for creating the KpnI restriction endonuclease cleavage site at nucleotide 31024, as has been done to create a wide variety of mutants having altered fiber phenotype.

c. Expression of Wild Type and Mutated Fiber Genes

A vaccinia virus expression system has been used to express wild type modified fiber proteins (Hong and Engler, 1991). The fiber genes from adenovirus serotypes 2 (31030 to 32778) and 5 were removed from the pUC119 plasmid (Vieira and Messing, 1987 "Production of single-stranded plasmid DNA". In *Methods in Enzymology*, R. Wu and L. Grossman, Eds., 1987, vol. 153, pp. 3–11 (Academic Press, San Diego)), by digestion with Asp718; in order to make the DNA ends blunt for cloning, the DNA was treated with a mixture of the four deoxyribonucleotide triphosphates (DATP, dCTP, dGTP, and dTTP) and the Klenow fragment of *E. coli* DNA polymerase I for 15 minutes at room temperature. Each DNA fragment was then ligated into the HpaI restriction endonuclease cleavage site in an expression vector (pTKgpt-3S; Falkner and Moss, 1988 *J. Virology* 62:1849–1854). When inserted into this site on the plasmid, expression of the fiber gene is under control of the p11 promoter, a promoter which is most actively transcribed at late times during infection. An advantage of this vector is that it allowed insertion of the fiber gene sequences by recombination into the thymidine kinase gene of wild type vaccinia virus; a second advantage is the ability to use positive selection with the *E. coli* gpt gene to enrich for recombinant viruses that contain the fiber gene.

Plaques that remained after two rounds of plaque purification were expanded and tested for production of fiber protein by infection of HeLa cells; lysates from these infected cells were tested for fiber protein expression on a Western blot developed with a monoclonal antibody that recognized fiber monomers and trimers. Alternatively, they could be screened for the presence of monomers or trimers using SDS-PAGE, as described in the following examples, since monomers migrate with a molecular weight of 62,000 Daltons and trimers migrate with a molecular weight of 180,000 Daltons.

Several recombinant vaccinia viruses that expressed large amounts of the fiber protein were recovered by this procedure. The protein that was produced by these recombinant viruses was identical to that obtained from adenovirus infection, as judged by the following criteria:

1. Reactivity to monoclonal and polyclonal antibodies that recognize fiber monomers and trimers (both on Western blots and by immune-precipitation).

2. Post-translational attachment of O-linked N-acetylglucosamine to the protein (measured by reactivity to a carbohydrate-specific antibody [RL-2; Holt et al., 1987 *J. Cell Biol.* 104:1157–1164; Mullis et al., 1990 *J. Virol.* 64:5317–5323, which has been widely distributed by Dr. Larry Gerace, Univ. of California at San Diego] and to labelling with bovine galactosyltransferase and UDP-[$^{14}$C]-galactose).

3. Reactivity on a Western blot developed with a monoclonal antibody [such as 2A6] that recognizes only correctly formed Ad2 and Ad5 fiber trimers.

4. Stability of the protein, for example, as judged by pulse-chase experiments.

Samples of fiber or fiber mutant proteins containing an extra six (PKRARP) (Seq. ID No. 3) or 27 (RIVNLLHVMFQSVYFSIAENFKSFFIQ) (Seq. ID No. 4) amino acids were loaded onto an 8% SDS-polyacrylamide gels. Samples were either boiled in 2% SDS at 100° C. for 3 minutes prior to loading (reduced) or left at room temperature in buffer containing 0.1% SDS (unreduced). After electrophoresis, the proteins were blotted onto nitrocellulose and the blots were developed with an antibody specific for fiber monomers and trimers.

The results show that the fiber mutants with the six amino acid insert formed trimers; the fiber mutants with the 27 amino acid insert did not.

Indirect immunofluorescence was also used to detect the formation of trimers. Hela cells infected with the recombinant vaccinia virus containing the fiber gene with the 27 amino acid insert at the C-terminus were fixed 24 hours after infection and the presence of fiber monomers and trimers detected with monoclonal antibodies specific for these forms. The results show that there is immunofluorescence with monoclonal antibodies that recognize either monomers or trimers; but no immunofluorescence with monoclonal antibodies that recognize only trimers of fiber protein.

EXAMPLE 2

Production of Functional Fiber Protein That Contains a Carboxyl-Terminal Linker Ad Which Continues to Form Functional Fiber Protein Trimers Methods The fiber gene from adenovirus type 5 was mutated by site-directed mutagenesis to add 30 extra nucleotides onto the end of the fiber open reading frame. An oligonucleotide (oligo 6796 5' CAAACGATTC TTATTAGGAT CCAGGGGCGG AAGCAGATGC GGAGGCTGAT GGTTCTTGGG CAATGTAT 3') (Seq. ID No. 5) was used for site-directed mutagenesis of the Ad5 fiber gene cloned into pUC119. This oligonucleotide was designed to add the nucleotides that encode the peptide (PASASASASPG) (Seq. ID No. 1) onto the end of the fiber gene open reading frame. This added segment included a BamHI restriction endonuclease cleavage site at the 3' end; which was subsequently used for insertion of new ligands, as described in Example 3. Insertion of this extra DNA segment was confirmed by DNA sequencing of the plasmid DNA.

The mutated DNA segment was removed from the plasmid by digestion with Asp718, made blunt-ended with the Klenow fragment of *E. coli* DNA Polymerase I (as described above), and cloned into the HpaI cleavage site in vector plasmid pTKgpt-3S. Recombinant vaccinia viruses that expressed this mutated fiber protein were isolated and plaque purified on HeLa cells. The fiber proteins that they expressed were characterized and compared to wild type protein as described above.

Results

The mutant proteins produced appear to be indistinguishable, based on 1. apparent molecular weight on denaturing polyacrylamide gels, and 2. ability to be recognized on Western blots by monoclonal antibodies that recognize fiber monomers (4D2) and that recognize correctly folded trimers (2A6).

EXAMPLE 3

Introduction of New Ligand Specificities into the Fiber Knob

Method

Short DNA segments containing new ligand specificities were constructed from synthetic DNA oligonucleotides. The ligand specificites chosen for study were a streptavidin mimic (Seq. ID No. 6 amino acid; Seq. ID No. 7 nucleotide), a biotin mimic (Seq. ID No. 8 amino acid; Seq. ID No. 9 nucleotide), angiotensin 2 (Seq. ID No. 10 amino acid; Seq. ID No. 11 nucleotide), and bombesin (gastrin release peptide) (Seq. ID No. 12 amino acid; Seq. ID No. 13 nucleotide).

These oligonucleotides were designed with BamHI cohesive ends that could be cloned into the BamHI cleavage site developed in Example 2. The specific amino acid sequence added to fiber in Example 2 was designed to extend the new ligand away from the bulk of the fiber protein, increasing its accessibility to the new receptor molecule. The resulting modified fiber protein included a linker and a ligand, and still formed a trimer.

This example demonstrates that non-viral ligands can be attached to the carboxyl terminus of the fiber protein via a peptide linker by expression of a genetically engineered nucleic acid sequence encoding the fiber protein, linker, and ligand.

Modifications and variations of the methods and compositions described herein will be obvious to those skilled in the art. Such modifications and variations are intended to come within the scope of the appended claims.

We claim:

1. A nucleic acid sequence encoding an adenovirus fiber protein and a peptide linker added to the carboxyl terminus of said adenovirus fiber protein, wherein said peptide linker is at least 6 but less than 27 amino acids long and said fiber protein forms a trimer when expressed in a mammalian cell.

2. The sequence of claim 1 wherein the fiber protein further comprises a ligand coupled to the linker.

3. The sequence of claim 1 wherein the fiber protein is altered to not bind to a specific targeted cell type.

4. The sequence of claim 1 wherein the linker peptide is PASASASASPGS (Seq. ID No. 1).

5. The sequence of claim 1 further comprising the adenovirus genes other than fiber protein encoding gene.

6. The sequence of claim 1 further comprising genes selected from the group consisting of genes encoding marker proteins, genes for gene therapy, and genes resulting in death of cells infected with the adenovirus.

7. The sequence of claim 2 wherein the ligand is selected from the group consisting of ligands specifically binding to a cell surface receptor and ligands that can be used to couple said fiber protein to other proteins.

8. The sequence of claim 7 wherein the fiber protein is altered to bind to a specific targeted cell type.

9. The sequence of claim 7 wherein the coupling ligands are selected from the group consisting of avidin binding proteins, biotin binding proteins, proteins bound by avidin, proteins bound by biotin, antibody proteins and fragments of antibody proteins.

* * * * *

SEQUENCE LISTING

<160> NUMBER OF SEQ ID NOS: 13

<210> SEQ ID NO 1
<211> LENGTH: 15
<212> TYPE: PRT
<213> ORGANISM: artificial sequence
<220> FEATURE:
<223> OTHER INFORMATION: linker peptide attached at the carboxyl end
      of the fiber protein

<400> SEQUENCE: 1

Ala Gln Glu Pro Ser Ala Ser Ala Ser Ala Ser Ala Pro Gly Ser
1               5                   10                  15

<210> SEQ ID NO 2
<211> LENGTH: 26
<212> TYPE: DNA
<213> ORGANISM: artificial sequence
<220> FEATURE:
<223> OTHER INFORMATION: oligonucleotide used to create a KpnI
      restriction endonuclease cleavage site at nucleotide 31024

<400> SEQUENCE: 2
ggcgcgtttc atggtacctg caacaa                                            26

<210> SEQ ID NO 3
<211> LENGTH: 6
<212> TYPE: PRT
<213> ORGANISM: artificial sequence
<220> FEATURE:
<223> OTHER INFORMATION: peptide that can be added to the c-terminus
      of the fiber protein without interfering with trimerization

<400> SEQUENCE: 3

Pro Lys Arg Ala Arg Pro
1               5

<210> SEQ ID NO 4
<211> LENGTH: 27
<212> TYPE: PRT
<213> ORGANISM: artificial sequence
<220> FEATURE:
<223> OTHER INFORMATION: peptide that if added to the c-terminus
      of the fiber protein prevents trimerization

<400> SEQUENCE: 4

Arg Ile Val Asn Leu Leu His Val Met Arg Gln Ser Val Tyr Phe
1               5                   10                  15

Ser Ile Ala Glu Asn Phe Lys Ser Phe Phe Ile Gln
                20                  25

<210> SEQ ID NO 5
<211> LENGTH: 51
<212> TYPE: DNA
<213> ORGANISM: artificial sequence
<220> FEATURE:
<223> OTHER INFORMATION: nucleotide sequence encoding the linker
      peptide attached at the carboxyl end of the fiber protein

<400> SEQUENCE: 5
gcccaagaac catcagcctc cgcatctgct tccgcccctg gatcctaata a                51

<210> SEQ ID NO 6
<211> LENGTH: 14
<212> TYPE: PRT

<213> ORGANISM: artificial sequence
<220> FEATURE:
<223> OTHER INFORMATION: amino acid sequence coding for streptavidin
      mimic that binds biotin

<400> SEQUENCE: 6

Gly Ser Cys Ser Gln Ala Pro Pro Lys Ala Ser Cys Gly Ser
            5                   10

<210> SEQ ID NO 7
<211> LENGTH: 36
<212> TYPE: DNA
<213> ORGANISM: artificial sequence
<220> FEATURE:
<223> OTHER INFORMATION: sequence coding for streptavidin mimic
      that binds biotin nucleotide sequence

<400> SEQUENCE: 7
gatcctgctc atgggcccca cctaaagctt cttgtg                             36

<210> SEQ ID NO 8
<211> LENGTH: 12
<212> TYPE: PRT
<213> ORGANISM: artificial sequence
<220> FEATURE:
<223> OTHER INFORMATION: amino acid sequence coding for biotin mimic
      that binds streptavidin

<400> SEQUENCE: 8

Gly Ser Ala Trp Arg His Pro Gln Phe Gly Gly Ser
            5                   10

<210> SEQ ID NO 9
<211> LENGTH: 30
<212> TYPE: DNA
<213> ORGANISM: artificial sequence
<220> FEATURE:
<223> OTHER INFORMATION: nucleotide sequence coding for biotin mimic
      that binds streptavidin

<400> SEQUENCE: 9
gatccgcttg gagacatcca caatttggcg                                    30

<210> SEQ ID NO 10
<211> LENGTH: 12
<212> TYPE: PRT
<213> ORGANISM: artificial sequence
<220> FEATURE:
<223> OTHER INFORMATION: amino acid sequence coding for angiotensin II
      peptide containing BaMHI cohesive ends

<400> SEQUENCE: 10

Gly Ser Asp Arg Val Tyr Ile His Pro Phe Gly Ser
            5                   10

<210> SEQ ID NO 11
<211> LENGTH: 30
<212> TYPE: DNA
<213> ORGANISM: artificial sequence
<220> FEATURE:
<223> OTHER INFORMATION: nucleotide sequence coding for angiotensin II
      peptide

<400> SEQUENCE: 11
gatccgatag agtttacatt catccatttg                                    30

<210> SEQ ID NO 12

```
<211> LENGTH: 14
<212> TYPE: PRT
<213> ORGANISM: artificial sequence
<220> FEATURE:
<223> OTHER INFORMATION: amino acid sequence coding for bombesin
      (gastrin release peptide) peptide containing BaMHI cohesive ends

<400> SEQUENCE: 12

Gly Ser Gly Asn His Trp Ala Val Gly His Leu Met Gly Ser
            5                   10

<210> SEQ ID NO 13
<211> LENGTH: 36
<212> TYPE: DNA
<213> ORGANISM: artificial sequence
<220> FEATURE:
<223> OTHER INFORMATION: nucleotide sequence coding for bombesin
      (gastrin release peptide) peptide

<400> SEQUENCE: 13
gatccggaaa ccattgggct gttggccacc ttatgg                          36
```